(12) United States Patent
Ray

(10) Patent No.: US 9,095,299 B2
(45) Date of Patent: Aug. 4, 2015

(54) SURGICAL SLEEVE SUCTION RETRACTOR

(76) Inventor: Stephen P. Ray, Trevor, WI (US)

( * ) Notice: Subject to any disclaimer, the term of this patent is extended or adjusted under 35 U.S.C. 154(b) by 195 days.

(21) Appl. No.: 13/453,032

(22) Filed: Apr. 23, 2012

(65) Prior Publication Data

US 2013/0281784 A1    Oct. 24, 2013

(51) Int. Cl.
*A61B 1/32* (2006.01)
*A61M 1/00* (2006.01)
*A61B 17/02* (2006.01)
*A61B 17/00* (2006.01)
*A61B 1/00* (2006.01)

(52) U.S. Cl.
CPC . *A61B 1/32* (2013.01); *A61B 17/02* (2013.01); *A61B 1/00094* (2013.01); *A61B 2017/0042* (2013.01); *A61B 2017/00353* (2013.01); *A61B 2017/00424* (2013.01); *A61B 2017/00429* (2013.01); *A61B 2217/005* (2013.01)

(58) Field of Classification Search
CPC ............... A61B 17/02; A61B 17/0218; A61B 2017/0212; A61B 2017/00353; A61B 2017/0042; A61B 2017/00424; A61B 2017/00429; A61B 2017/00433; A61B 2017/00438; A61B 2017/00446; A61B 2017/348; A61B 2017/3482; A61B 2017/3484; A61B 1/32; A61B 1/00071; A61B 1/00075; A61B 1/0008; A61B 1/00094; A61M 29/00
USPC ......... 600/201, 204–206, 210, 213, 217, 226, 600/235
See application file for complete search history.

(56) References Cited

U.S. PATENT DOCUMENTS

| | | | |
|---|---|---|---|
| 5,885,292 A * | 3/1999 | Moskovitz et al. | 606/79 |
| 8,603,105 B2 * | 12/2013 | Sauer | 606/119 |
| 8,608,719 B2 | 12/2013 | Ray | |
| 8,617,130 B2 | 12/2013 | Ray | |
| 2005/0222538 A1 * | 10/2005 | Embry et al. | 604/181 |
| 2009/0192603 A1 * | 7/2009 | Ryan | 623/2.11 |
| 2012/0083658 A1 * | 4/2012 | Hahn et al. | 600/205 |
| 2012/0143241 A1 | 6/2012 | Ray | |
| 2013/0267786 A1 * | 10/2013 | Vayser et al. | 600/205 |
| 2013/0281961 A1 | 10/2013 | Ray | |
| 2013/0296817 A1 | 11/2013 | Ray | |

FOREIGN PATENT DOCUMENTS

WO  PCT/US2013/037714    4/2013

* cited by examiner

*Primary Examiner* — Michael T Schaper
*Assistant Examiner* — Tracy Kamikawa
(74) *Attorney, Agent, or Firm* — Lesavich High-Tech Law Group, S.C.; Stephen Lesavich

(57) ABSTRACT

A hollow disposable sleeve suction retractor. The sleeve suction retractor is an ergonomically shaped combination suction/retractor instrument for holding and retracting tissues, suctioning tissue pieces, blood and fluids and a surgical smoke plume from an electrosurgery device all at the same time. The suction sleeve retractor is comfortable to hold securely and allows a surgeon a clear line of sight on an area of tissue dissection. It can be used without the need for having another hand (e.g., surgeon's or an assistant, etc.) sponge or separate suction devices in a wound. It is economical to purchase and does not have to be sterilized or autoclaved since it disposable.

17 Claims, 5 Drawing Sheets

SIDE VIEW

SIDE VIEW

SIDE VIEW

SIDE VIEW

SIDE VIEW

TOP VIEW

SURGICAL SLEEVE SUCTION RETRACTOR

FIELD OF THE INVENTION

This invention relates to surgical instruments. More specifically, it relates to a hollow, disposable surgical sleeve suction retractor.

BACKGROUND OF THE INVENTION

"Electrosurgery" is the application of a high-frequency electric current to biological tissue as a means to cut, coagulate, desiccate, or fulgurate tissue. Electrosurgery includes the ability to make precise cuts with limited blood loss. In electrosurgical procedures, tissue is heated by an electric current Electrosurgery is performed using an electrosurgical generator, also referred to as a "power supply" or "waveform generator" and a hand piece including one or several electrodes, sometimes referred to as an "RF Knife" or a "Bovie," after the inventor.

"Electrocauterization" is a type of electrosurgery and includes the process of destroying tissue using heat conduction from a metal probe heated by electric current. The procedure is also used to stop bleeding from small vessels (larger vessels being ligated) or for cutting through soft tissue.

Electrosurgery and electrocauterization techniques are used in the treatment of cancers via electrodesiccation and curettage. Electrosurgery and electrocauterization techniques produce surgical smoke.

"Surgical smoke" generated from electrosurgery and electrocauterization techniques include carbonized tissue, blood, and virus aerosols. In addition, surgical smoke includes gases such as benzene, toluene, formaldehyde, and polycyclic aromatic hydrocarbons that are known carcinogens. These gases also create an "acrid smell" in an operating room.

Another danger from surgical smoke comes from the particle content of the smoke. Particulate smoke posses serious health risks to surgical teams and is similar to second hand smoke from cigarettes.

Another danger from surgical smoke is the transmission of diseases. The AIDS epidemic has focused attention on the routes by which HIV virus may be transmitted. One potential exposure route is inhalation of blood-containing "aerosols" infected with the virus in the operating room. The potential hazard of blood aerosol generated by electrosurgery is from surgical tools capable of generating a wide distribution of particle sizes produced blood-containing particles in the respirable range. Surgical masks typically do not provide adequate respiratory protection against these aerosols produced in surgical smoke.

A "retractor" is a surgical instrument that is used to hold back underlying organs and tissues, so that body parts under the incision may be accessed. It is also used to separate the edges of a surgical incision or wound. Surgical retractors are available in many sizes, shapes, and styles. Surgical retractors are used in different surgical procedures. Retractors are used during operations to help doctors by moving tissue and organs away from the area upon which the surgery is to be performed.

Surgical retractors are very important because they determine the exposure of the operative field. A surgeon needs an exposure best as possible while inflicting a minimum of trauma to the surrounding tissue. The handles of the retractor may be hook shaped, notched, or ring shaped to give the holder a firm grip without tiring. The blades of the retractors are at a right angle to the shaft. The blades can be smooth, raked, or hooked.

Surgical retractors are non-hollow components made from materials that are sterilizable and autoclavable so they may be reused for multiple, successive surgical procedures. A common material used in the making of retractors is stainless steel. Stainless steel is preferred because of its strength and its ability to be sterilized.

However, there are several drawbacks of stainless steel retractors. Stainless steel instruments are expensive to purchase and time consuming to maintain. They become very slippery when they come into contact with blood and other body fluids which can lead to tissue damage during operation. Moreover, stainless steel is also thermally highly conductive which also results in tissue injury as it quickly absorbs heat from the tissue with which it comes in contact. Another disadvantage is that they have reflective surfaces which produce glare under the high level illumination which is very common during surgical procedures.

Generally, there are two types of retractors, self-retaining and hand-held. "Self-retaining" retractors do not need an assistant to hold them in place (e.g., a rib spreader, etc.). "Hand-held" retractors require an assistant to hold them. A hand-held retractor is held by its handle properly so as to produce maximum exposure of the surgical area, maximum leverage, and steady retraction.

During breast surgery and other soft tissue surgery a surgeon has to have fraction on the tissue edge being dissected. Tissue retractors hold tissue flaps away from the treatment site. This provide better visibility, reach and undisturbed working. However, when retractors known in the art used on breast tissues and other soft tissues, such tissues are likely to bleed, tear or rip when retracted.

"Suction" is the flow of a fluid into a partial vacuum, or region of low pressure. The pressure gradient between this region and the ambient pressure will propel matter toward the low pressure area. Typically during most surgeries, a drainage tube is inserted into the wound and attached to a suction device such as an external suction pump to remove subcutaneous fluid, blood and tissue.

There are several problems associated with suction tube devices. The heads on suction tubes often get clogged when larger pieces of tissue are sucked into the device. Suction tubes and devices are very difficult to keep clean and sanitary. They typically require cleaning with brushes and other instruments. They also must be sterilizable and autoclavable. Suction devices are very noisy, especially when multiple suction devices are used. Multiple suction devices contribute to noise pollution in an operating room.

During surgery on soft tissues a surgeon would typically use an electrosurgery device for cutting or dissecting, one or more retractors and one or more suction devices. The surgeon is typically assisted by one or more assistants (e.g., other surgeons, nurses, medical technicians, etc.)

The surgeon has to have fraction on the tissue edge being dissected. At the same time the surgeon is cutting usually with an electrosurgery device that produces a surgical smoke plume that requires a separate suction device held in the wound to evacuate the smoke. Another suction device is used to remove blood, fluids and tissue pieces.

When a wound is narrow or under a flap of tissue (e.g., near a breast nipple) it is very awkward for an assistant to hold a retractor, a separate suction device that effectively evacuates the smoke, and another for blood and irrigating fluids that does not get in the surgeon's line of site.

In a deeper wound it can be difficult for the surgeon to get fraction on the tissue due to the size of the surgeon's hands, the slippery surface of gloves on the one or more retractors or the bulk of sponges that are used to gain a friction hold on the surface of a slippery tissue.

Thus, it is desirable to solve some of the many problems associated with medical instruments used for surgery on soft tissues and other types of human tissues.

SUMMARY OF THE INVENTION

In accordance with preferred embodiments of the present invention, some of the problems associated with surgery on soft tissues are overcome. A surgical sleeve suction retractor is presented.

The suction sleeve retractor is an ergonomically shaped combination suction/retractor instrument for holding and retracting tissues, suctioning, tissues, blood and fluids and a surgical smoke plume from an electrosurgery device all at the same time. The suction sleeve retractor is comfortable to hold securely and allows a surgeon a clear line of sight on an area of dissection during a surgery. It is easy to use in a narrow cut or under a flap of tissue. It can be used without the need for having another hand (e.g., surgeon's or an assistant, etc.) sponge or separate suction devices in a wound. It is economical to purchase and does not have to be sterilized or autoclaved since it disposable.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein.

DETAILED DESCRIPTION OF THE INVENTION

Figure 1A:
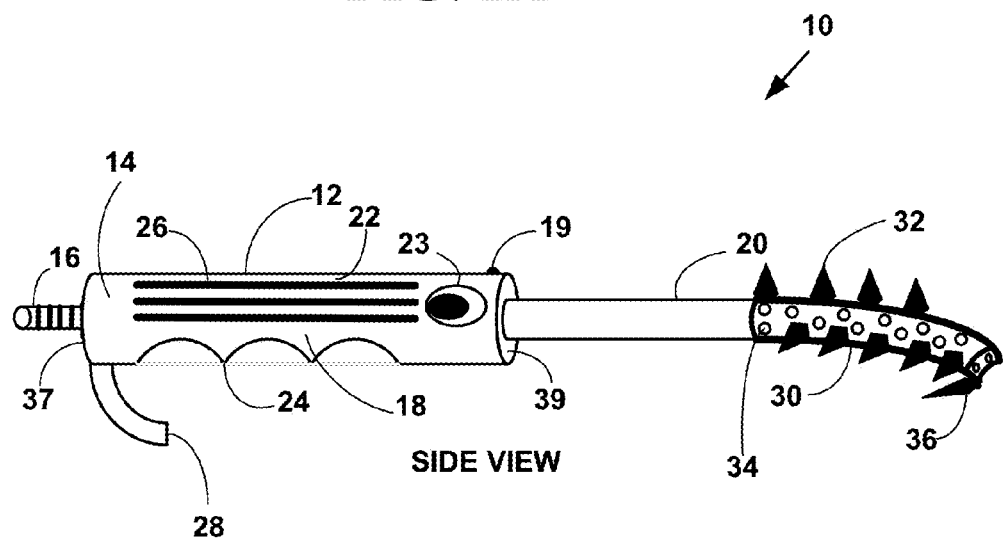
FIG. 1A is a block diagram illustrating a side view of a sleeve suction retractor.

FIG. 1A is a block diagram illustrating a side view 10 of a disposable surgical sleeve suction retractor 12. The sleeve suction retractor 12 includes a circular hollow body portion 14, a first end component 16, an ergonomic handle portion 18, plural grasping protrusions 19, a second end component 20 and a gripping indented component 23. However, the present invention is not limited to these components and more, fewer or other components can be used to practice the invention.

Figure 1B:
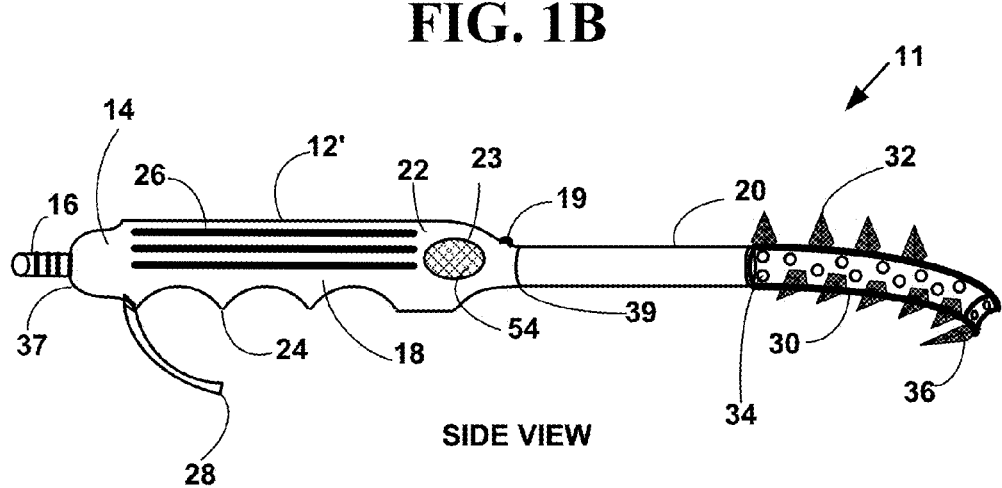
FIG. 1B is a block diagram illustrating side view of the sleeve suction retractor.

FIG. 1B is a block diagram illustrating a side view 11 of the disposable surgical sleeve suction retractor 12'. The sleeve suction retractor 12' includes an oval hollow body portion 14, a first end component 16, an ergonomic handle portion 18, plural grasping protrusions 19, a second end component 20 and a gripping indented component 23.

The hollow body portion 14 provides an instrument core. The hollowing body portion 14 is also used to evacuate suctioned materials.

The first end component 16 is connected to a first end 37 of the hollow body portion 14 and comprises a hollow connector for attaching to suction tubing connected to an external suction source and used to provide a source of suction during a surgery.

The ergonomic handle portion 18 comprises a middle body portion of the hollow body portion 14 with a top surface 22 and a bottom surface 24 designed for right or left-handed gripping and allows for easy control of the traction on a tip of a retractor/suction surface on the second end component 20. The top surface 22 includes a pre-determined pattern of plural protrusions 26 for gripping and to assist with control rotation motions and wrist motions of a user. The bottom surface 24 includes a pre-determined pattern specifically sized and shaped for comfortable gripping by a human hand.

A protrusion component 28 on the bottom surface 24 of the ergonomic handle portion 18 is adjacent to the first end component 16 and helps keep the human hand from sliding off the ergonomic handle portion 18 during backward pulling during retraction during surgery.

The plural grasping protrusions 19 are located on the top surface 22 (See FIG. 6 for additional detail) of the hollow body portion 14 opposite the first end component 16 and located adjacent to the second end component 20 of the hollow body portion 14.

The plural grasping protrusions 19 are oriented ninety degrees to a horizontal axis of the hollow body portion 14 and are on the top surface 22 of hollow body portion, thereby providing a griping surface for allowing and facilitating a backward pull on the hollow body portion 14 for adjustment and removal when the disposable sleeve surgical suction retractor 12 has been interested in incision during surgery.

The second end component 20 is a hollow component connected to a second end 39 of the hollow body portion 14 including a hollow curved portion with an angle varying from about one degree to about thirty degrees providing an optimal angle for retracting a pre-determined type of tissue. However, the present invention is not limited to these angles and other angles can be used to practice the invention.

The second end component 20 includes a combination retraction/suction component 30 for providing simultaneous retraction and suction during the surgery.

A retraction portion of the retraction/suction component 30 includes plural retraction protrusions 32 arranged in a pre-determined pattern for providing tissue retraction during the surgery.

A suction portion of the retraction/suction component 30 includes plural suction components 34 arranged in a predetermined pattern for providing suction of fluids and solids (e.g., tissues pieces, etc.) during the surgery.

The plural indented gripping components 23 (only one of which is illustrated in the side view of FIG. 1) located adjacent to the plural grasping protrusions 19 on a front side and a back side of the ergonomic handle portion 18 allowing placement of a thumb and index finger of the user to grip and securely when pulling back on a combination retraction/suction component portion 30 of the second end component 20.

In one embodiment, the plural indented components 23 may further include additional gripping surfaces such as cross-hatching 54, or other types of raised services (e.g., oval, circular, trapezoidal, etc.) as described herein. However, the present invention is not limited to these materials and other materials can be used to practice the invention.

In one embodiment, the sleeve suction retractor 12 is a hollow, integral, one-piece device with no detachable components. In another embodiment, the sleeve suction retractor 12 includes one or more detachable components.

Figure 1C:
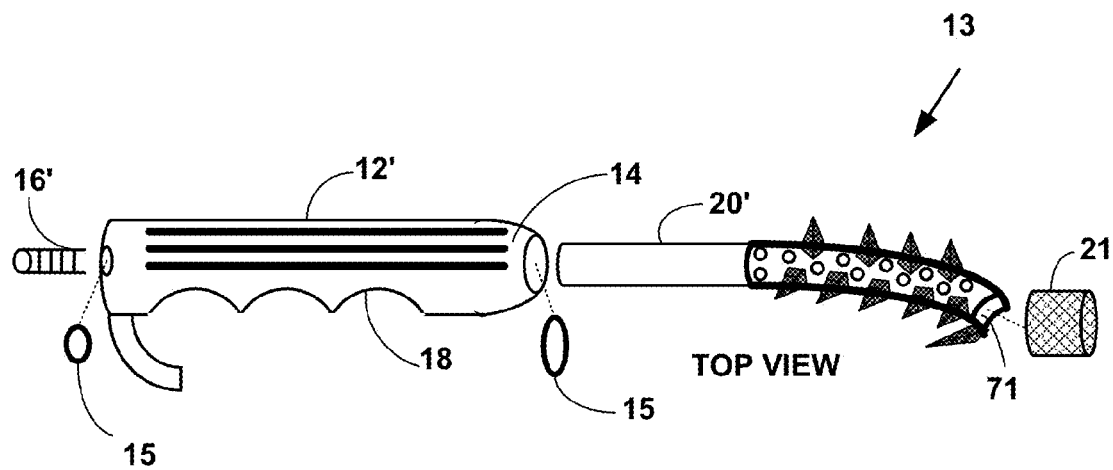
FIG. 1C is a block diagram illustrating a side view of a sleeve suction retractor with a detachable/connectable first end component and a detachable/connectable second end component.

FIG. 1C is a block diagram 13 illustrating a sleeve suction retractor 12' with a detachable/connectable first end component 16' and/or a detachable/connectable second end component 20'.

In FIG. 1C the sleeve suction retractor 13 is used with only a detachable/connectable first end component 16' and/or only with a detachable/connectable second end component 20' or with both components detachable.

In one embodiment, all components and portions of the device 12 are created from Polyetherimide, Polyimide other thermosetting polyimides, other plastics and/or composite materials. However, the present invention is not limited to these materials and other materials can be used to practice the invention.

"Polyetherimide" (PEI) is an amorphous, amber-to-transparent thermoplastic with characteristics similar to the related plastic PEEK. Polyether ether ketone (PEEK) is a colorless organic polymer thermoplastic Relative to PEEK, PEI is cheaper, but less temperature-resistant and lower in impact strength.

For example, commercially, ULTEM is a family of PEI products manufactured by SABIC. ULTEM resins are used in medical and chemical instrumentation due to their heat resistance, solvent resistance and flame resistance.

"Polyimide" (PI) is a polymer of imide monomers. Such imide monomers include pyromellitic dianhydride and 4,4'-oxydianiline and others. Polyimide materials are lightweight, flexible, resistant to heat and chemicals. Polyimide parts are not affected by commonly used solvents and oils, including hydrocarbons, esters, ethers, alcohols and freons. They also resist weak acids.

"Thermosetting polyimides" are known for thermal stability, good chemical resistance, excellent mechanical properties. Normal operating temperatures for such polymides range from cryogenic with temperatures below about −238° F. (−150° C.) to those exceeding about 500° F. (260° C.).

"Composite materials" are engineered or naturally occurring materials made from two or more constituent materials with significantly different physical or chemical properties which remain separate and distinct at the macroscopic or microscopic scale within the finished structure. Common polymer-based composite materials, include at least two parts, a substrate (e.g., fibers, etc.) and a resin.

The composite materials include "Fiber-reinforced polymers" (FRP) including thermoplastic composites, short fiber thermoplastics, long fiber thermoplastics or long fiber-reinforced thermoplastics. There are numerous thermoset composites, but advanced systems usually incorporate aramid fiber and carbon fiber in an epoxy resin matrix. The composite materials also include carbon/carbon composite materials with carbon fibers and a silicon carbide matrix.

However, the present invention is not limited to these materials and other materials can be used to practice the invention.

In one embodiment, one or more portions of the device 12 and/or second end component 20 are constructed from Polyvinyl chloride (PVC) polyethylene and/or polypropylene. However, the present invention is not limited to these materials and other materials can be used to practice the invention.

The sleeve suction retractor 12 is constructed from an economical material as a hollow, integral one-piece device and is intended to be a single-use, disposable device. The device comes in a sterile package that is opened and used during a surgery. When the surgery is finished, the device 12 is thrown away.

Since device 12 is hollow and constructed from a plastic and/or composite material, it is lighter in weight (e.g., a few ounces (grams) in weight, etc.) than most metal retractors making it easier to use for long periods during a surgery. The device 12 has better thermodynamic characteristics than metal retractors, do not have reflective surfaces that produce glare and are not as slippery as metal retractors.

The sleeve suction retractor 12 may be injection molded, extruded, pultruded, pull-winded, cast, and/or manufactured and/or produced with other techniques.

"Extrusion" is a manufacturing process where a material is pushed through a die to create long objects of a fixed cross-section. Hollow sections are usually extruded by placing a pin or mandrel in the die. Extrusion may be continuous (e.g., producing indefinitely long material) or semi-continuous (e.g., repeatedly producing many shorter pieces). Some extruded materials are hot drawn and others may be cold drawn.

Feedstock for extrusion may be forced through the die by various methods: by an auger, which can be single or twin screw, powered by an electric motor; by a ram, driven by hydraulic pressure, oil pressure or in other specialized processes such as rollers inside a perforated drum for the production of many simultaneous streams of material.

"Pultrusion" is a continuous process for manufacture of materials with a constant cross-section. Reinforced fibers are pulled through a resin, possibly followed by a separate preforming system, and into a heated die, where the resin undergoes polymerization. Pultrusion is not limited to thermosetting polymers or polymides. More recently, pultrusion has been successfully used with thermoplastic matrices such either by powder impregnation of fibers or by surrounding it with sheet material of a thermoplastic/polymide matrix, which is then heated.

In one embodiment, components of the sleeve suction retractor 12 are produced with an overwrapping transverse winding process that combines continuous filament winding with a pultrusion manufacturing process to produce a pultruded pullwound hollow cylindrical structure with the shape of hollow cylindrical structure that is used for components in device 12.

The "pullwinding" process incorporates plural longitudinal reinforcement fibrers with plural helical-wound (e.g., hoop, etc.) layers, providing maximum torsional properties and hoop strength. A self-contained inline winding unit is used with a pultrusion machine for feeding angled fibers between layers of unidirectional fibers before curing in a pultrusion die. The plural longitudinal re-enforcement fibers are used for axial and bending resistance while the plural helical-wound fibers are used for hoop tension and compression resistance. The pullwinding equipment is comprised of twin winding heads which revolve in opposite directions over a spindle. However, the present invention is not limited to such an embodiment and other embodiments can also be used to practice the invention.

In another embodiment, the sleeve suction retractor 12 is constructed from surgical stainless steel, other metals, plastic, ceramics, composite material and/or other materials, and/or combination thereof and is re-usable, autoclavable and sterilizable. However, the present invention is not limited to such an embodiment and other embodiments can also be used to practice the invention.

In one embodiment, the sleeve suction retractor 12 is cast and includes zirconium dioxide ($ZrO_2$; also known as zirconia) ceramics. Ceramic sleeve suction retractors 12 will not corrode in harsh surgical environments, are non-magnetic, and do not conduct electricity. Because of their resistance to strong acid and caustic substances, and their ability to retain an edge longer than metal, ceramic the sleeve suction retractor 12 are more suitable than metal sleeve suction retractor 12. However, the present invention is not limited to such an embodiment and other embodiments can also be used to practice the invention.

The first end component 16 includes a hollow connector for attaching to suction tubing used during surgery. The first end component 16 includes a smooth bubble connector, a stepped connector (e.g., about 3/16"-1/2" (about 4.76 mm-12.7 mm) and/or smaller and/or larger size) and/or a "Y" shaped connector for connecting to standardized sized surgical and hospital tubing.

However, the present invention is not limited to these hollow connectors and other hollow connectors can be used to practice the invention.

In another embodiment, the first end component 16' is a detachable/connectable portion that can changed to provide different types of connectors to the suction tubing.

In such an embodiment, the first end component 16' includes a screw connection means, a snap connection means and/or pin-lock connection means and/or other connection means.

Such detachable/connectable portions may require the use of an "O" ring 15 (FIG. 1C) or other type of sealing gasket and/or sealing component comprising a rubber, silicon, composite material and/or other type of material. The "O" ring is used to ensure the detachable/connectable first end component 16' provides a proper seal when connected to the hollow body portion 14 so the device 12 does not lose suction power when connected to an external suction device.

A "screw connection means" is a type of fastener characterized by a helical ridge on a first component, known as an external thread wrapped around a second component. Screw threads in the first component are designed to mate with a complementary thread, known as an internal thread on a second component.

A "snap connection means" includes one or more bulbous protrusions on the hollow body portion 12 that engage one or more bulbous depressions in the first end component 14. In another embodiment, the snap connection means includes one or more bulbous protrusions on the first end component that engage one or more bulbous depressions on the hollow body portion 12.

The "pin-lock connection means" includes plural pins on the first end component 12 and the hollow body portion 12 includes plural pin receptacles for engaging and locking the plural pins when twisted. In another embodiment, the pin-lock connection means includes plural pins on the hollow body portion 12 and the first end component 14 includes plural pin receptacles for engaging and locking the plural pins.

In one embodiment flat rectangular pins are used on the pin-lock connection means. However, the present invention is not limited to this embodiment and other shapes (e.g., circular, oval, square, trapezoid etc.) can also be used to practice the invention.

Various other types connection means can be used to keep the first end component 16 and the hollow body portion 14 connected. However, the present invention is not limited to the embodiments describes and more, fewer and other equivalent connection means embodiments can also be used to practice the invention.

FIG. 1A illustrates a "stepped" connector comprising the first end component 16. However, the present invention is not limited to this hollow connector and other hollow connectors can be used to practice the invention.

Figure 2A:
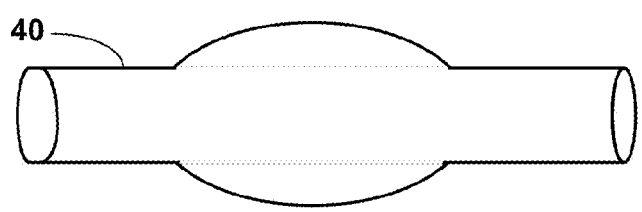
FIG. 2A is a block diagram illustrating a side view of a smooth bubble connector for the sleeve suction retractor.

FIG. 2A is a block diagram 38 illustrating a smooth bubble connector 40 for first end component 16. The drawing is not drawn to scale and is drawn larger to illustrate details. However, the present invention is not limited to this hollow connector and other hollow connectors can be used to practice the invention.

Figure 2B:
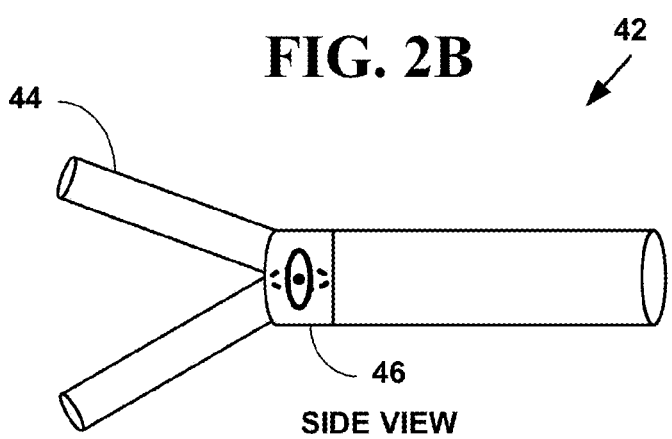
FIG. 2B is a block diagram of illustrating a side view of a "Y" shaped connector for the sleeve suction retractor.

FIG. 2B is a block diagram 42 illustrating a "Y" shaped connector 44 for the first end component 16. The "Y" shaped connector 44 is used for connecting two section sources and may further include a valve 46 to switch between two suction sources (e.g., high power and lower power suction, etc.). The drawing is not drawn to scale and is drawn larger to illustrate details. However, the present invention is not limited to this hollow connector and other hollow connectors can be used to practice the invention.

"Ergonomics" is a good 'fit' between a user, equipment and their environments. Ergonomics takes account of the user's capabilities and limitations in seeking to ensure that tasks, functions, information, safety and the environment suit each user. Ergonomic devices are produced to lower a number of or prevent injuries from using the device.

The ergonomic handle portion 18 is designed for right or left-handed gripping and allows for easy control of the traction on the tip of a retractor surface on the second end 20.

The ergonomic handle portion 18 includes the top surface 22 and the bottom surface 24.

The top surface 22 includes a pre-determined pattern of protrusions 26 orientated along a horizontal axis of the top surface. The pre-determined pattern of protrusions 26 assist with control rotation motions or wrist of the user. In one embodiment, the protrusions are circular and/or oval and/or trapezoidal in shape. The protrusions prevent slipping yet are comfortable to grip for long periods of time during a very long surgery. The pre-determined pattern includes protrusions of a same shape or combinations thereof of different shapes. However, the present invention is not limited to such an embodiment and more, fewer or other types of protrusions can be used to practice the invention.

In another embodiment, the top surface 22 includes a pre-determined cross-hatch pattern 54. The cross-hatch pattern 54 includes a pre-determined pattern of two or mores sets of intersecting parallel protrusions. One or more of the sets of intersecting parallel lines protrude up and away from the top surface. Cross-hatch patterns are often used on filing tools used in the construction industry. The protrusions on the cross-hatch pattern provide a non-slip gripping surface on the handle 18.

In one embodiment, the cross hatch 54 protrusions are square, rectangular, circular and/or oval and/or trapezoidal in shape. The pre-determined pattern includes protrusions of a same shape or combinations thereof of different shapes. However, the present invention is not limited to such an embodiment and more, fewer or other types of protrusions can be used to practice the invention.

Figure 3A:
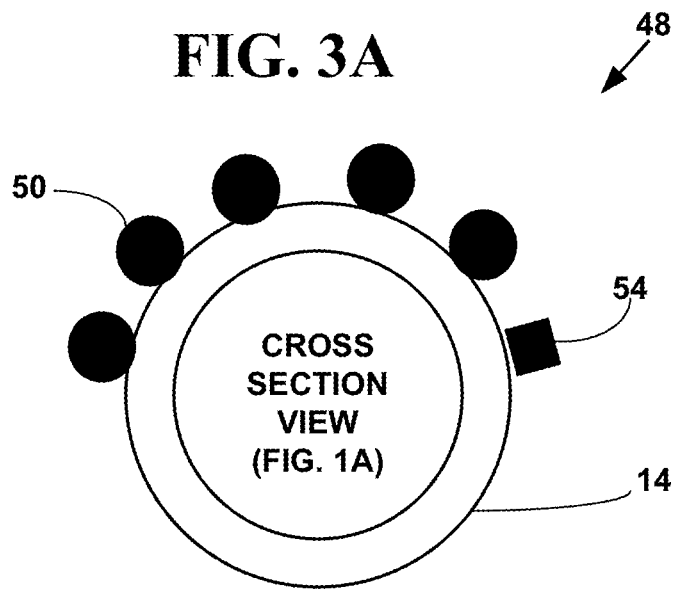
FIG. 3A is a block diagram illustrating a side view of a circular shaped ergonomic handle portion with circular protrusions.

FIG. 3A is a block diagram illustrating a cross section view 48 of a circular shaped or round shaped ergonomic handle portion 18 with circular protrusions 50. (Not drawn to scale and drawn larger to illustrate details). However, the present invention is not limited to such an embodiment and more, fewer or other types of shapes and protrusions can be used to practice the invention.

Figure 3B:
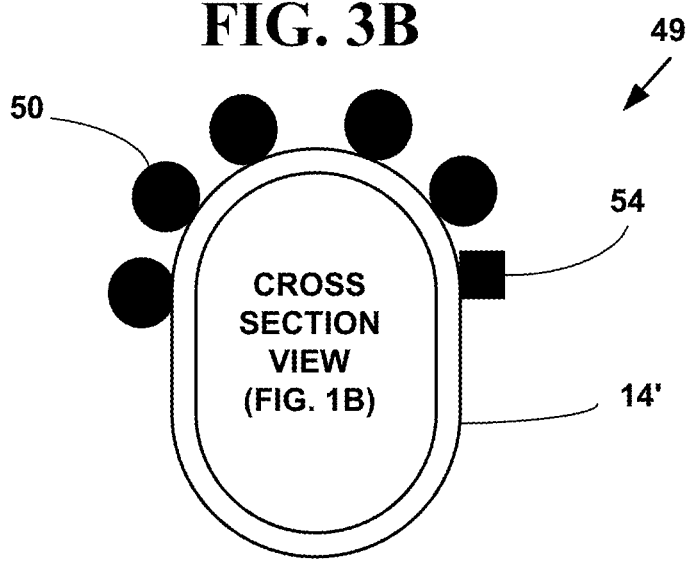
FIG. 3B is a block diagram illustrating a side view of an oval shaped ergonomic handle portion with circular protrusions.

FIG. 3B is a block diagram illustrating a cross section view 48 of an oval shaped ergonomic handle portion 18 with circular protrusions 50. (Not drawn to scale and drawn larger to illustrate details). However, the present invention is not limited to such an embodiment and more, fewer or other types of shapes and protrusions can be used to practice the invention.

Figure 4:
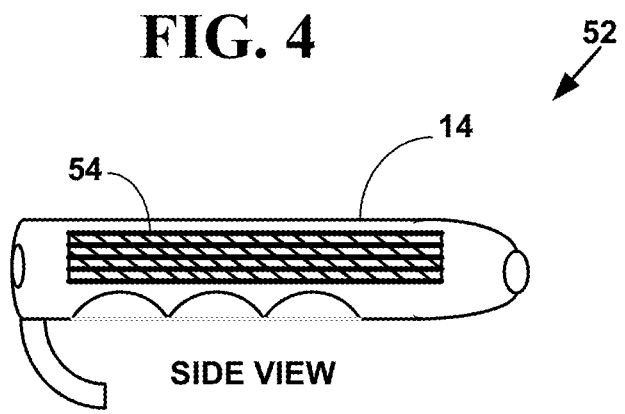
FIG. 4 is a block diagram illustrating a side view of the ergonomic handle portion with a cross hatch pattern.

FIG. 4 is a block diagram illustrating side view 52 of the ergonomic handle portion 18 with a cross hatch pattern 54. In FIG. 4 the sets of horizontal lines protrude up and away from the ergonomic handle portion 18 as is illustrated by square 54 in the cross section view in FIG. 3. In another embodiment, other than the sets of horizontal lines protrude up and away from the ergonomic handle portion 18.

In another embodiment, the surface other than the bottom surface 24 of the ergonomic handle portion 18 includes the cross-hatching 54 pattern to provide additional gripping and non-slipping functionality. However, the present invention is not limited to such an embodiment and more, fewer or other types of gripping/non-slip surfaces can be used to practice the invention.

Returning to FIG. 1A the ergonomic handle portion 18 has a bottom surface 24 in a "wave" pattern specifically sized and shaped to be gripped by a human hand. The wave pattern includes plural wave crests and wave depressions between the wave crests for engaging human fingers comfortably for gripping. However, the present invention is not limited to such an embodiment and more, fewer or other types of gripping shapes and patterns can be used to practice the invention.

The ergonomic handle portion 18 further includes a protrusion component 28 on the bottom surface 24 of back end of the handle 18 adjacent to the first end component 16 that helps keep a hand from sliding off the handle 18 during backward pulling during retraction.

The protrusion component 28 includes a curved shape, hook shape, a ring and/or other shape. FIG. 1 illustrates a curved shaped protrusion 28. However, the present invention is not limited to such an embodiment and more, fewer or other types of protrusions can be used to practice the invention.

The gripping indented component 23 is located near the front end of the ergonomic handle portion 18 and allows an index finger and thumb of the user to grip and securely hold the device 12 when pulling back on the retractor portion of the second end component 20 while the middle, ring and little finger of the user grip the bottom surface 24 of the ergonomic handle 18 to allow a downward pressure on the retractor/suction tip of the second end component 20.

The plural gripping protrusions 19 (See FIG. 6) are located opposite the first end component 16 and adjacent to the second end component 20 of the handle 18 are 90 degrees in orientation to a horizontal axis of the hollow body portion 14 on a top surface of the hollow body portion 14. The plural gripping protrusions 19 allow and facilitate a backward pull on the device 12 for adjustment and removal during a surgery. The plural gripping protrusions 19 may also include cross-hatching between individual protrusions.

In one embodiment, the plural gripping protrusions 19 are located only on a top surface 22 of the handled 18. In another embodiment, the plural gripping protrusions circle the entire handle 18. However, the present invention is not limited to such an embodiment and more, fewer or other combinations of surfaces for the protrusions 19 can be used to practice the invention.

In one embodiment, the plural protrusions 19 are circular and/or oval and/or trapezoidal in shape. The plural protrusions of a same shape or combinations thereof of different shapes. However, the present invention is not limited to such an embodiment and more, fewer or other types of protrusions can be used to practice the invention.

Figure 5:
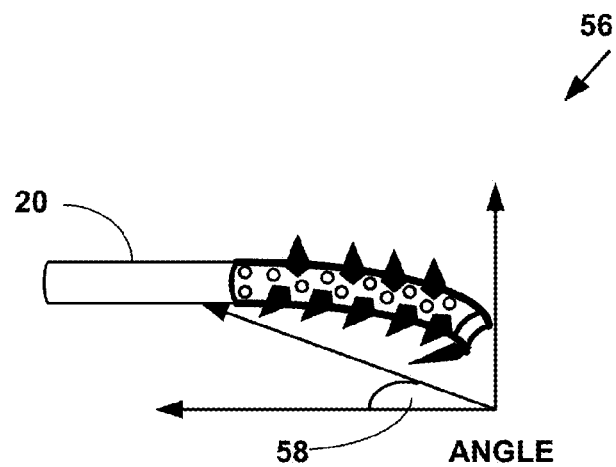
FIG. 5 is a block diagram illustrating a side view of an angle of a second end component.

FIG. 5 is a block diagram illustrating a side view 56 of an angle 58 of a second end component 20.

The second end portion 20 is a hollow curved portion with an angle 58 varying from about one degree to about thirty (1°-30°) degrees. The curved portion provides an optimal angle for retracting a pre-determined type of tissue. However, the present invention is not limited to such an embodiment and more, fewer or other angles can be used to practice the invention.

FIG. 5 illustrates only an angle 58 for the retraction/suction component 30. However, the whole second end portion 20 can include a first angle and the retraction/suction component 30 can be oriented at the same angle and/or a different angle.

The second end portion 20 includes a combination retraction/suction component 30. A retraction portion of the retraction/suction component 30 includes plural retraction protrusions 32 arranged in a pre-determined pattern. A suction portion of the retraction/suction component 30 includes plural suction components 34 arranged in a pre-determined pattern.

Figure 6:
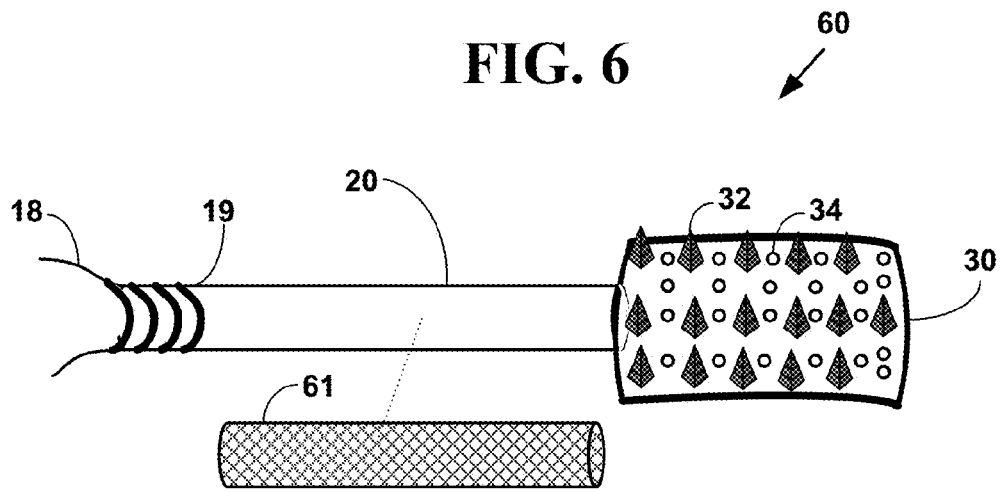
FIG. 6 is a block diagram illustrating a top view of the retraction/suction component.
Figure 7:
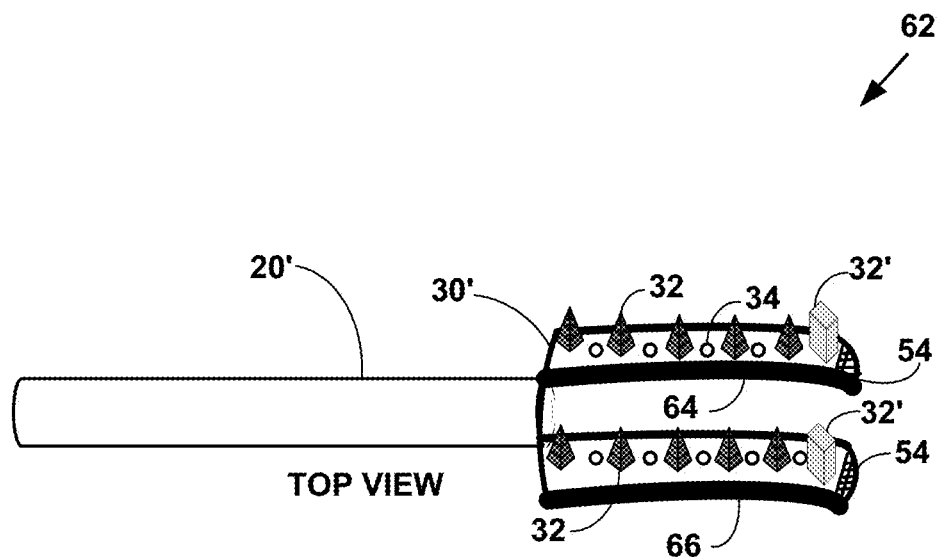
FIG. 7 is a block diagram illustrating a top view of a retraction/suction component with plural retraction/suction components.

As is illustrated in FIG. 1A FIG. 6, and FIG. 7, the retraction portion 30, 30' includes plural pyramid 32 and/or trapezoidal shaped protrusions 32' which are displaced at an angle from about one degree to about eighty degrees (1°-80°) from a surface of the second end portion 20, 20'. Such angles allow grasping and holding and retraction of a tissue without ripping or tearing the tissue or causing any further trauma or injury to the tissue. In one embodiment, the plural pyramid shaped protrusions may each include additional plural protrusions (e.g., angular teeth, etc.) for additional gripping. However, the present invention is not limited to such an embodiment and more, fewer or other types of protrusions, shapes and angles can be used to practice the invention.

In another embodiment, all and/or selected ones of the plural protrusions 32 may be replaced with the cross-hatching 54 described above (See FIG. 8). However, the present invention is not limited to such an embodiment and more, fewer or other types of protrusions, shapes and angles can be used to practice the invention.

The suction portion 34 includes a plural circular and/or oval shaped openings 34. However, the present invention is not limited to such an embodiment and more, fewer or other types of openings and shapes can be used to practice the invention. The suction openings are used to suction surgical smoke, tissue particles, blood and fluids simultaneously as a tissue is retracted and grasped by the retraction portions 30.

During a surgery the tissue surrounding the wound area typically gets suctioned onto the surface of the working tip and cuts off the suction. There are also particles of fat at the operative site. When the wound is irrigated the fat is suspended in the fluids. It is important to remove the fat particles. However, the fat clogs the openings on the suction tips and stops or slows the flow of removing the fluid.

The retraction/suction component 30 further includes a larger suction opening 71 (FIG. 1C) to remove fat particles.

If a surgery does not generate many fat particles, the larger suction opening 71 may further include a tip covering 21 (FIG. 1C), such as a plastic, metal, ceramics and/or composite material, mesh and/or screen and/or gauze to prevent suctioning up large pieces of tissue or fat and clogging the end 15 of the suction tip. Tip covering 21 is not drawn to scale to illustrate details. However, the present invention is not limited to such an embodiment and other embodiments can also be used to practice the invention.

In one embodiment, the tip covering 21 includes an attachable/removeable multi-layer gauze sleeve. In another embodiment the tip covering 21 includes a plastic mesh. The tip covering 21 is composed of three to four layers of coarse knit, non-shedding, gauze. However, the present invention is not limited to such an embodiment and more, fewer or other types of materials can be used to practice the invention.

The tip covering 21 is narrower at the tip and wider at the opening so it conforms snuggly to the shape of the device 12. It is held on the device 12 in part by the conforming friction. The tip covering 21 is replaced on the larger suction opening 71 as often as needed when the gauze became clogged with particulate matter that couldn't be wiped off.

Included on a proximal end of the tip covering 21 is a small radio-opaque non-shedding cloth strip. This would allow visualization of the tip covering 21 by x-ray, in the event a sleeve count was off at the end of the surgery. A portable x-ray of the wound would show the tip covering 21 if it were present anywhere in the patient being operated on. However, the present invention is not limited to such an embodiment and more, fewer or other types of tip covering 21 materials can be used to practice the invention.

The retraction/suction component 30 includes an alternating pattern of retraction protrusions 32 and suction components 34, one retraction protrusion 32, one suction component 34, another retraction protrusion 23, another retraction protrusion, etc. In another embodiment, the pre-determined pattern includes alternating rows and/or columns of retraction protrusions 32 and rows and/or columns of suction components 34. However, the present invention is not limited to such an embodiment and more, fewer or other types of pre-determined patterns can be used to practice the invention.

Returning to FIG. 1, the retraction/suction component 30 further includes an extended tip component 36 for further engaging and holding a tissue. The tip component includes one or more larger retractor protrusions 32. The extended tip component 36 is displaced at an angle from about one degree to about eighty degrees (1°-80° from a surface of the second end portion 20. Such angles allow additional grasping and holding of a tissue without ripping or tearing the tissue or causing any further trauma or injury to the tissue. However, the present invention is not limited to such an embodiment and more, fewer or other types of protrusions, shapes and angles can be used to practice the invention.

FIG. 6 is a block diagram illustrating a top view 60 of the retraction/suction component 30. The plural grasping protrusions 19 are visible in FIG. 6.

In another embodiment, the retraction/suction component 30 includes plural separated retraction/suction components 30 at a same or different angles of orientation. Such devices are used for specific types of surgeries.

FIG. 7 is a block diagram illustrating a top view 62 of a retraction/suction component 30' with plural separated retraction/suction components 64, 66 (only two of which are illustrated for simplicity). A portion of each of the plural separated retraction/suction components 64, 66 includes cross-hatching 54. However, the present invention is not limited to such an embodiment and more, fewer or other types of protrusions, shapes and angles can be used with the plural retraction/suction components to practice the invention.

Figure 8:
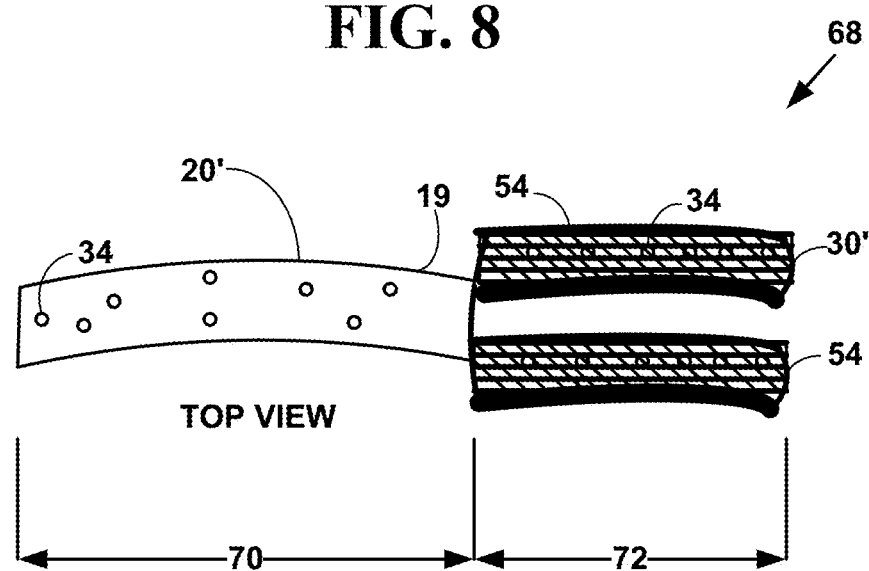
FIG. 8 is a block diagram illustrating a top view the second end component with cross-hatching retraction components.

FIG. 8 is a block diagram illustrating a top view 68 the second end component 20' with cross-hatching 54 retraction components. In this embodiment, all of the plural retraction protrusions 32 are replaced with cross-hatching 54 as was described above. The cross-hatching 54 provides a different type of tissue grasping/retraction capability and typically creates less damage to sensitive tissue types during a surgery. However, the invention is not limited to this embodiment and other embodiments may be used to practice the invention.

In another embodiment, second end component 20' includes a first portion 70 and a second portion 72 including the retraction/suction component 30'. Both portions are bendable and configurable to change an angle of retraction/suction component 30' as is illustrated in FIG. 8. In such an embodiment, the first portion 70 and/or the second portion 72 may be constructed of PVC, other plastic, composite material and/or other material so it can be bent into a desired shape and/or angle and when bent, have a shape and/or angle maintained. However, the invention is not limited to this embodiment and other embodiments may be used to practice the invention.

In another embodiment portions of the second end component 20' not including the combination retraction/suction component 30 may also include plural suction components 34 for additional suction capabilities as is illustrated in FIG. 8. However, the invention is not limited to this embodiment and other embodiments may be used to practice the invention.

In another embodiment, the second end component 20' is a detachable/connectable portion that can changed to provide different types of angles and retractors for different types of tissues and different types of surgeries.

For example, a first type of the second end component 20' includes a specific size and shape and angle for breast surgery. A second type of the second end component 20' includes a second specific size and shape and angle for heart surgery, etc. Thus, the device 12 provides a large amount of flexibility for different types of surgeries.

In one embodiment the second end component 20' and the retraction/suction component 30' is made of the same material as first end component 16, hollow body 14 and ergonomic handle component 18. In another embodiment the second end component 20' and the retraction/suction component 30' are made of different materials than first end component 16, hollow body 14 and ergonomic handle component 18 to allow for bending into a desired shape and/or angle.

When an embodiment is detachable/connectable, the second end portion 20' includes a screw connection means, a snap connection means and/or pin-lock connection means as was described above for the first end portion 16. The second end portion 20' may also include an "O" ring 15 or other sealing component as was described for the first end portion 16 to provide an appropriate seal for suction. However, the present invention is not limited to such an embodiment and more, fewer or other types of connection means for the second end portion 20 can be used to practice the invention.

In another embodiment, second end portion 20' is constructed from surgical stainless steel, other metals, plastic, ceramics, composite material and/or other materials, and/or combination thereof and is re-usable, autoclavable and sterilizable. In such an embodiment, the hollow body portion 14 is a one-time use, disposable component and the second end portion 20' is a multi-use, non-disposable portion.

In another embodiment, the hollow body portion 14 is constructed from surgical stainless steel, other metals, ceramics, plastic, composite material and/or other materials, and/or combination thereof and is re-usable, autoclavable and sterilizable. In such an embodiment, the second end portion is a one-time use, disposable component.

In one embodiment, when an embodiment is detachable/connectable, the second end portion 20' may include a attachable/removeable sleeve cover 61 (FIG. 6). In another embodiment, the cover 61 includes a plastic mesh.

However, the present invention is not limited to such embodiments and more, fewer or materials can be used to practice the invention.

The sleeve cover 61 provides an frictional surface to further improve gripping of the device 12 by a user. Included on a proximal end of the cover 61 would also be a small radio-opaque non-shedding cloth strip for x-ray detection as was described above (e.g., tip cover 17, FIG. 1B).

However, the present invention is not limited to such embodiments and more, fewer or other combinations can be used to practice the invention.

In another embodiment, the hollow body portion 14 (both with and without a detachable/connectable first end component 16) are both constructed from surgical stainless steel, other metals, plastic, composite material and/or other materials, and/or combination thereof and are re-usable, autoclavable and sterilizable.

The hollow disposable surgical suction sleeve retractor 12 described herein is an ergonomically shaped combination suction/retractor instrument for simultaneously holding and retracting tissues, suctioning tissue pieces, blood and fluids and a suctioning surgical smoke plume from an electrosurgery device all at the same time.

The device 12 reduces gases and aerosols created by the electrosurgery devices making an operating room safer and more pleasant for the medical personal. It also helps reduce and eliminate heat transfer problems to tissues being operating on, slipping and glare that are common from most metal retractors. By eliminating at least one suction device, noise pollution is also significantly reduced in the operating room.

Since the suction sleeve retractor is hollow, ergonomic and lighter than metal retractors, it is light in weight and comfortable to hold securely and allows a surgeon a clear line of sight on an area of tissue dissection. It can be used without the need for having another hand (e.g., surgeon's or an assistant, etc.) sponge or separate suction devices in a wound. It is easy to use in a narrow cut or under a flap of tissue. It is economical to purchase and does not have to be sterilized or autoclaved since it disposable.

The device 12 was described for use with surgery for humans. However, the device can also be used for surgery on animals and is not limited to surgery for humans and can be used for surgeries on other entities (e.g., animals, plants, etc.).

It should be understood that the architecture, processes, methods and devices described herein are not related or limited to any particular type of materials or design unless indicated otherwise. Various types of materials and designs may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, materials and angles may be used other than those described, and more or fewer elements may be used in the block diagrams that describe any devices.

While various elements of the preferred embodiments have been specifically described as being implemented in specific designs and materials, in other embodiments other designs and materials may alternatively be used, and vice-versa.

The claims should not be read as limited to the described order or elements unless stated to that effect. In addition, use of the term "means" in any claim is intended to invoke 35 U.S.C. §112, paragraph 6, and any claim without the word "means" is not so intended.

Therefore, all embodiments that come within the scope and spirit of the following claims and equivalents thereto are claimed as the invention.

I claim:

1. A hollow, integral, disposable sleeve surgical suction retractor, comprising in combination:
   a hollow body portion providing an instrument core and providing an evacuation component for materials suctioned during a surgery;
   a first end component connected to a first end of the hollow body portion comprising a hollow connector for attaching to suction tubing connected to an external suction source and used to provide a source of suction during the surgery;
   a second end component with a combination retraction and suction component;
   an ergonomic handle portion comprising a middle body portion of the hollow body portion with a top surface and a bottom surface designed for right or left-handed gripping and allowing for easy control of traction on a tip of a combination retraction and suction surface on the combination retraction and suction component, the top surface including a pre-determined pattern of a plurality of protrusions for gripping and assisting with control of rotation motions of a wrist of a user, the bottom surface including a pre-determined gripping pattern specifically sized and shaped for comfortable gripping by a hand of the user and further including a protrusion component on the bottom surface of the ergonomic handle portion adjacent to the first end component that helps keep the hand of the user from sliding off the ergonomic handle portion during backward pulling and during retraction;
   a plurality of indented gripping components located adjacent to a pre-determined pattern of a plurality of grasping protrusions on a front side and on a back side of the ergonomic handle portion allowing placement of a thumb and an index finger of the user to grip securely when pulling back on the combination retraction and suction component of the second end component with the combination suction and retraction component;
   the pre-determined pattern of the plurality of grasping protrusions located on the ergonomic handle portion opposite the first end component and located adjacent to the second end component with the combination retraction and suction component, wherein the pre-determined pattern of the plurality of grasping protrusions is oriented ninety degrees to a horizontal axis of the ergonomic handle portion and is located on the top surface of the ergonomic handle portion, thereby providing a gripping surface, allowing and facilitating a backward pull on the ergonomic handle portion for adjustment and removal when the disposable sleeve surgical suction retractor has been inserted into an incision during the surgery;
   the second end component with the combination retraction and suction component connected to a second end of the hollow body portion including a hollow curved portion, the hollow body portion and the hollow curved portion forming an angle therebetween from one degree to thirty degrees providing an optimal angle for grasping, holding and retracting a pre-determined type of tissue and including the combination retraction and suction component for providing simultaneous grasping holding, retraction and suction during the surgery;

a tissue grasping, holding and retraction portion of the combination retraction and suction component including a plurality of angular tissue grabbing, holding and retraction protrusions arranged in a pre-determined pattern in a longitudinal direction along an exterior surface from a first end of the tissue grasping, holding and retraction portion to a second end of the tissue grasping, holding and retraction portion for providing tissue grasping, holding and retraction during the surgery, wherein the predetermined pattern of the plurality of angular tissue grabbing, holding and retraction protrusions includes an alternating pattern alternating between individual angular tissue grabbing, holding and retraction protrusions and individual suction components;

a suction portion of the combination retraction and suction component including a plurality of the suction components arranged in the pre-determined pattern in a longitudinal direction from a first end of the suction portion to a second end of the suction portion for providing the suction of the materials including surgical smoke, fluids and solids during the surgery; and an extended tip component on the combination retraction and suction component for further engaging and holding the tissue during the surgery.

2. The hollow, integral, disposable sleeve surgical suction retractor of claim 1 wherein the disposable sleeve surgical suction retractor is constructed from polyetherimide, polyimide, other thermosetting polyimides, composite materials, Polyvinyl chloride (PVC), polyethylene, polypropylene or combinations thereof.

3. The hollow, integral, disposable sleeve surgical suction retractor of claim 1 wherein the first end component comprises a hollow stepped, smooth bubble or a "Y" shaped connector.

4. The hollow, integral, disposable sleeve surgical suction retractor of claim 1 wherein the bottom surface of the ergonomic handle portion includes a wave pattern with a plurality of wave crests and wave troughs for engaging fingers of the user.

5. The hollow, integral, disposable sleeve surgical suction retractor of claim 1 wherein the plurality of protrusions on the top surface of the ergonomic handle portion includes circular, oval, trapezoidal or square shaped protrusions oriented along the top surface.

6. The hollow, integral, disposable sleeve surgical suction retractor of claim 1 wherein the plurality of protrusions on the top surface of the ergonomic handle portion includes cross-hatching protrusions comprising one or more sets of parallel lines protruding from the top surface.

7. The hollow, integral, disposable sleeve surgical suction retractor of claim 1 wherein the plurality of grasping protrusions located on the top surface of the ergonomic handle portion includes circular, oval or trapezoidal shaped protrusions.

8. The hollow, integral, disposable sleeve surgical suction retractor of claim 1 wherein the plurality of grasping protrusions located on the top surface of the ergonomic handle portion includes cross-hatching protrusions comprising one or more sets of parallel lines protruding from the ergonomic handle portion.

9. The hollow, integral, disposable sleeve surgical suction retractor of claim 1 wherein the plurality of retraction protrusions includes pyramidal or trapezoidal shaped protrusions.

10. The hollow, integral, disposable sleeve surgical suction retractor of claim 1 wherein the plurality of suction components includes circular or oval shaped suction components.

11. The hollow, integral, disposable sleeve surgical suction retractor of claim 1 wherein the hollow body portion, first end component, ergonomic handle portion and the plurality of grasping protrusions are constructed from polyetherimide, polyimide, other thermosetting polyimides or composite materials and the second end component is constructed from Polyvinyl chloride (PVC), polyethylene, or polypropylene to allow bending of the second end component to a pre-determined shape or the optimal angle.

12. The hollow, integral, disposable sleeve surgical suction retractor of claim 1 further including an attachable and detachable tip cover for a suction tip of the combination retraction and suction component of the second end component with the combination retraction and suction component, wherein the tip cover includes a small radio-opaque non-shedding cloth strip for x-ray detection.

13. A hollow sleeve surgical suction retractor, comprising in combination:

a hollow body portion providing an instrument core and providing an evacuation component for materials suctioned during a surgery;

a detachable and attachable first end component connected to a first end of the hollow body portion comprising a hollow connector for attaching to suction tubing connected to an external suction source and used to provide a source of suction during the surgery;

a detachable and attachable second end component with a combination retraction and suction component;

an ergonomic handle portion comprising a middle body portion of the hollow body portion with a top surface and a bottom surface designed for right or left-handed gripping and allowing for easy control of traction on a tip of a retractor surface on the combination retraction and suction component, the top surface including a pre-determined pattern of a plurality of protrusions for gripping and assisting with control of rotation motions of a wrist of a user, the bottom surface including a pre-determined pattern specifically sized and shaped for comfortable gripping by a hand of the user and further including a protrusion component on the bottom surface of the ergonomic handle portion adjacent to the first end component that helps keep the hand of the user from sliding off the ergonomic handle portion during backward pulling and during retraction;

a plurality of indented gripping components located adjacent to a pre-determined pattern of a plurality of grasping protrusions on a front side and on a back side of the ergonomic handle portion allowing placement of a thumb and an index finger of the user to grip securely when pulling back on the combination retraction and suction component of the detachable and attachable second end component with the combination retraction and suction component;

the pre-determined pattern of the plurality of grasping protrusions located on the ergonomic handle portion opposite the first end component and located adjacent to the detachable and attachable second end component with the combination retraction and suction component, wherein the pre-determined pattern of the plurality of grasping protrusions is oriented ninety degrees to a horizontal axis of the ergonomic handle portion and is on the top surface of the ergonomic handle portion, thereby providing a gripping surface, allowing and facilitating a backward pull on the ergonomic handle portion for adjustment and removal when the disposable sleeve surgical suction retractor has been inserted into an incision during the surgery; and the detachable and attachable second end component with the combination retraction and suction component connected to a second end of the hollow body portion including a hollow curved portion, the hollow body portion and the hollow curved portion forming an angle therebetween from about one degree to about thirty degrees providing an optimal angle for grasping, holding and retracting a pre-determined type of tissue and including the combination retraction and suction component for providing simultaneous grasping, holding, retraction and suction during the surgery;

a retraction portion of the combination retraction and suction component including a plurality of angular tissue grabbing, holding and retraction protrusions arranged in a pre-determined pattern in a longitudinal direction along an exterior surface from a first end of the retraction portion to a second end of the retraction portion for providing tissue grasping, holding and retraction during the surgery;

a suction portion of the combination retraction and suction component including a plurality of suction components arranged in a pre-determined pattern in a longitudinal direction from a first end of the suction portion to a second end of the suction portion for providing the suction of the materials including surgical smoke, fluids and solids during the surgery; and an extended tip component on the combination retraction and suction component for further engaging and holding the tissue during the surgery.

14. The hollow sleeve surgical suction retractor of claim 13 wherein the detachable and attachable second end component includes a sleeve cover to provide a frictional surface for improved gripping and includes a small radio-opaque non-shedding cloth strip for x-ray detection.

15. The hollow sleeve surgical suction retractor of claim 13 wherein the plurality of angular tissue grabbing, holding and retraction protrusions includes a plurality of pyramid or trapezoidal shaped protrusions protruding from surfaces of the retraction portion of the combination retraction and suction component of the detachable and attachable second end component.

16. The hollow sleeve surgical suction retractor of claim 13 wherein the detachable and attachable second end component includes a set of different detachable and attachable second end components including a plurality of different combination retraction and suction components with different angles and with different shapes and including different combination retraction and suction components with a single contiguous surface or a plurality of separated surfaces suitable for different types of surgeries on different types of tissues.

17. The hollow sleeve surgical suction retractor of claim 13 wherein the disposable sleeve surgical suction retractor constructed from surgical stainless steel.

* * * * *